US010180371B2

United States Patent
Duerr et al.

(10) Patent No.: US 10,180,371 B2
(45) Date of Patent: Jan. 15, 2019

(54) ULTRASONIC DETECTOR WITH STORABLE PROBES

(71) Applicant: Spectronics Corporation, Westbury, NY (US)

(72) Inventors: John Duerr, Massapequa Park, NY (US); Richard Regan, Short Hills, NJ (US); Robert E. Cannuscio, West Chester, PA (US)

(73) Assignee: Spectronics Corporation, Westbury, NY (US)

(*) Notice: Subject to any disclaimer, the term of this patent is extended or adjusted under 35 U.S.C. 154(b) by 126 days.

(21) Appl. No.: 15/474,314

(22) Filed: Mar. 30, 2017

(65) Prior Publication Data

US 2017/0299460 A1 Oct. 19, 2017

Related U.S. Application Data

(60) Provisional application No. 62/318,969, filed on Apr. 6, 2016.

(51) Int. Cl.

| G01M 3/24 | (2006.01) |
|---|---|
| G01H 3/12 | (2006.01) |
| G10K 11/35 | (2006.01) |
| G01M 3/00 | (2006.01) |
| G01N 29/22 | (2006.01) |
| G01N 29/24 | (2006.01) |

(52) U.S. Cl.
CPC .............. *G01M 3/24* (2013.01); *G01H 3/12* (2013.01); *G01N 29/22* (2013.01); *G01N 29/226* (2013.01); *G01N 29/24* (2013.01); *G10K 11/35* (2013.01); *G01M 3/007* (2013.01); *G01M 3/246* (2013.01)

(58) Field of Classification Search
CPC ...... G01N 29/22; G01N 29/226; G01N 29/24; G01N 29/2481
See application file for complete search history.

(56) References Cited

U.S. PATENT DOCUMENTS

| 4,987,769 | A | * | 1/1991 | Peacock | .................. | G01M 3/24 |
| | | | | | | 73/40.5 A |
| 5,445,026 | A | * | 8/1995 | Eagan | ..................... | G01H 3/12 |
| | | | | | | 73/40.5 A |

(Continued)

OTHER PUBLICATIONS

Spectronics Corporation: Operator's Manual, "Marksman II Series Ultrasonic Diagnostic Tool", 17 pgs. (Jun. 2014).

(Continued)

*Primary Examiner* — Daniel S Larkin
*Assistant Examiner* — Anthony W Megna Fuentes
(74) *Attorney, Agent, or Firm* — Drinker Biddle & Reath LLP

(57) ABSTRACT

An ultrasonic detector has a housing containing a transducer, a battery or other power supply, and any other necessary electronics. At a front end of the housing is a socket into which one of a plurality of interchangeable probes can be inserted. At the rear end of the housing, there is a handle by which an operative can hold the detector in use. On the inside of the housing, extending at least partially into the handle, is an elongate chamber within which at least one probe can be stored. A cover of the handle closes a rear end of the probe storage chamber and can be removed to expose a portion of the probe storage chamber and allow a probe to be inserted or removed.

16 Claims, 3 Drawing Sheets

(56) References Cited

U.S. PATENT DOCUMENTS

| | | | | |
|---|---|---|---|---|
| 6,234,021 B1* | 5/2001 | Piety | ............... | G01H 1/00 |
| | | | | 73/592 |
| 8,495,914 B2* | 7/2013 | Izikoff | ............... | G01M 3/243 |
| | | | | 73/40.5 A |
| 2005/0126264 A1* | 6/2005 | Komninos | ............... | G01M 3/24 |
| | | | | 73/40.5 A |
| 2009/0303058 A1* | 12/2009 | Goodman | ............... | G01M 3/24 |
| | | | | 340/605 |
| 2010/0039271 A1* | 2/2010 | Izikoff | ............... | G01M 3/24 |
| | | | | 340/605 |
| 2010/0097057 A1* | 4/2010 | Karpen | ............... | G01N 21/8806 |
| | | | | 324/238 |
| 2011/0169481 A1* | 7/2011 | Nguyen | ............... | H01M 2/1055 |
| | | | | 324/126 |

OTHER PUBLICATIONS

Spectronics Corporation: Product literature, "MDE-2000NC Marksman II", 1 pg. (Apr. 29, 2015).

Spectronics Corporation: Product literature, "Spectroline Marksman II Ultrasonic Diagnostic Tool", 2 pgs. (Jan. 2012).

\* cited by examiner

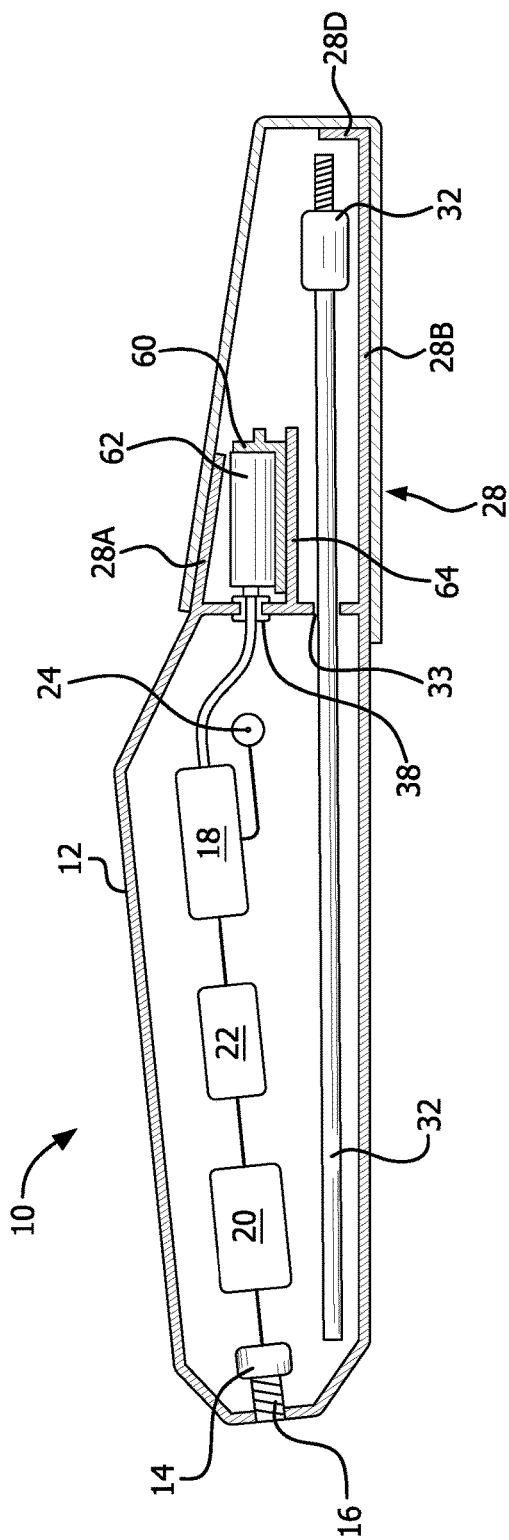
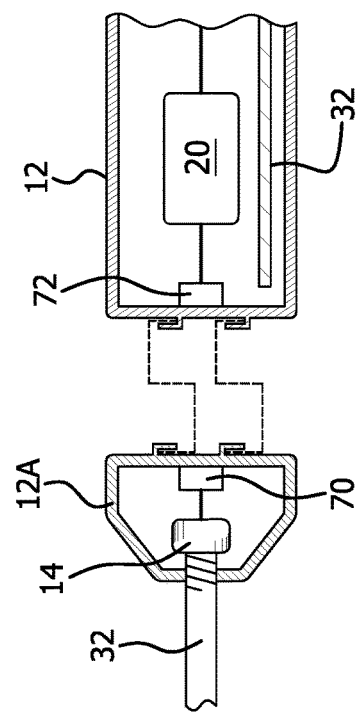
FIG. 3
FIG. 4

ULTRASONIC DETECTOR WITH STORABLE PROBES

FIELD OF THE INVENTION

The invention relates to passive ultrasonic detectors, especially for the detection of leaks and other mechanical problems in machinery.

BACKGROUND OF THE INVENTION

It has previously been proposed to detect certain types of mechanical problem by sensing distinctive sounds that they produce, especially ultrasonic sounds. For example, a fluid leak from a pressurized system can produce a hissing sound, and a failing bearing can produce a grinding sound. In order to detect ultrasonic sound, it is necessary for the sound to be fed to a transducer that will convert it to frequencies that are audible to the human operative. When inspecting machinery, this typically involves a handheld device containing the transducer, and having at its front end a probe that can be placed near to, or in contact with, the machinery that is to be inspected.

Different probes are usually preferred for contact with the machinery and for air pickup near the machinery. A contact probe is typically a solid rod of material that transmits the ultrasonic frequencies of interest. An air probe is typically a tube that guides the sound in air to the transducer, while excluding extraneous noises.

Detectors with interchangeable probes have previously been proposed. One example of such a detector is sold by the assignees of the present application under the trademark Spectroline® Marksman II. A disadvantage of most detectors with interchangeable probes is that a separate carrying case is necessary to contain the detector and the various probes. That can be inconvenient when working in the field, because the operative may want to change from one probe to the other in places where it is inconvenient to bring the carrying case or to set down the carrying case in order to take out one probe and put away another probe.

There is, therefore, a need for a more compact and portable handheld ultrasonic detector.

SUMMARY OF THE INVENTION

According to one embodiment of the invention, there is provided an ultrasonic detector comprising a housing containing a transducer, a battery or other power supply, and any other necessary electronics. At a front end of the housing is a socket into which one of a plurality of interchangeable probes can be inserted. At the rear end of the housing, there is a handle by which an operative can hold the detector in use. On the inside of the housing, extending at least partially into the handle, is an elongate chamber within which at least one probe can be stored. A cover of the handle closes a rear end of the probe storage chamber and can be removed to expose a portion of the probe storage chamber and allow a probe to be inserted or removed.

Preferably, the probe storage chamber is sufficiently wide to contain all of the probes provided with the detector, or at least to contain all except one of the probes.

Removing the handle cover may also expose other devices that are not usually needed while actually using the detector, for example, a port for a battery charger, a data port for reprogramming the detector, or a battery compartment.

Devices that are commonly needed while actually using the detector, for example, a socket for headphones and any controls and displays needed by the operative, may be provided on top or side surfaces of the housing.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 3 is a longitudinal cross-sectional view through the detector of FIG. 1.

FIG. 4 is a partial cross-sectional view of an alternate embodiment of the invention with a removable front portion.

DETAILED DESCRIPTION

Figure 1:
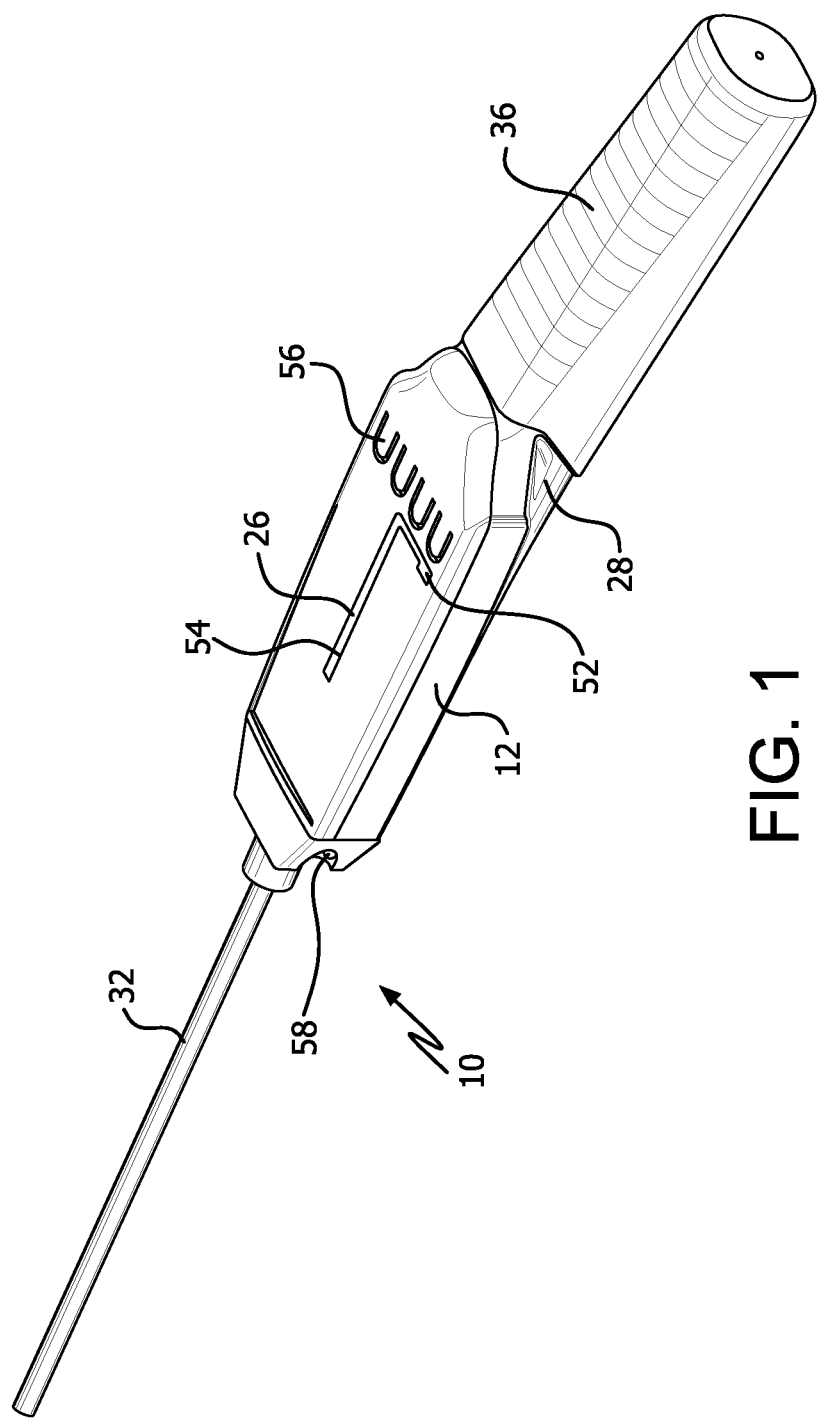
FIG. 1 is a perspective view of an embodiment of an ultrasonic detector with a probe installed.

Reference will now be made in detail to various embodiments of the present invention, an example of which is illustrated in the accompanying drawings.

Referring to the drawings, one form of ultrasonic detector, indicated generally by the reference numeral 10, comprises a housing 12 having at or near its front end an ultrasonic transducer 14 with a socket 16 into which a base end of a probe 32 can be inserted. The socket 16 may be provided with screw threading, a bayonet connector, or any other convenient mechanism for releasably securing the probe in its operating position. The interior of the housing 12 may contain a microprocessor controller 22, an amplifier 20, an adapter 18 for a headphone socket and/or data port 24 on the exterior of the housing 12, and/or any other convenient electrical or electronic equipment, such as conventional noise control electronics to detect and reduce ambient noise, and self-adjusting automatic gain control circuitry to enhance sensitivity and simplify operation. A display 26 may be provided on the exterior of the housing 12 for displaying information related to the sensed signal or other features of the detector (e.g., battery power). As shown, the display 26 may contain an LED 52 indicating that the device is powered on and a row of LEDs 54 for indicating a sensitivity setting. A light or pair of lights 58 may be provided at the front of the housing 12 to illuminate a work area around the tip of the probe.

The housing 12 may also have switches 56 for turning the detector 10 on or off, raising or lowering the sensitivity or other variable setting, and turning on or off the lights 58. The LEDs 52, 54 and the switches 56 may be covered by a cover sheet 59 (shown in FIG. 2) with appropriate transparent and flexible areas and with explanatory or decorative markings.

Figure 2:
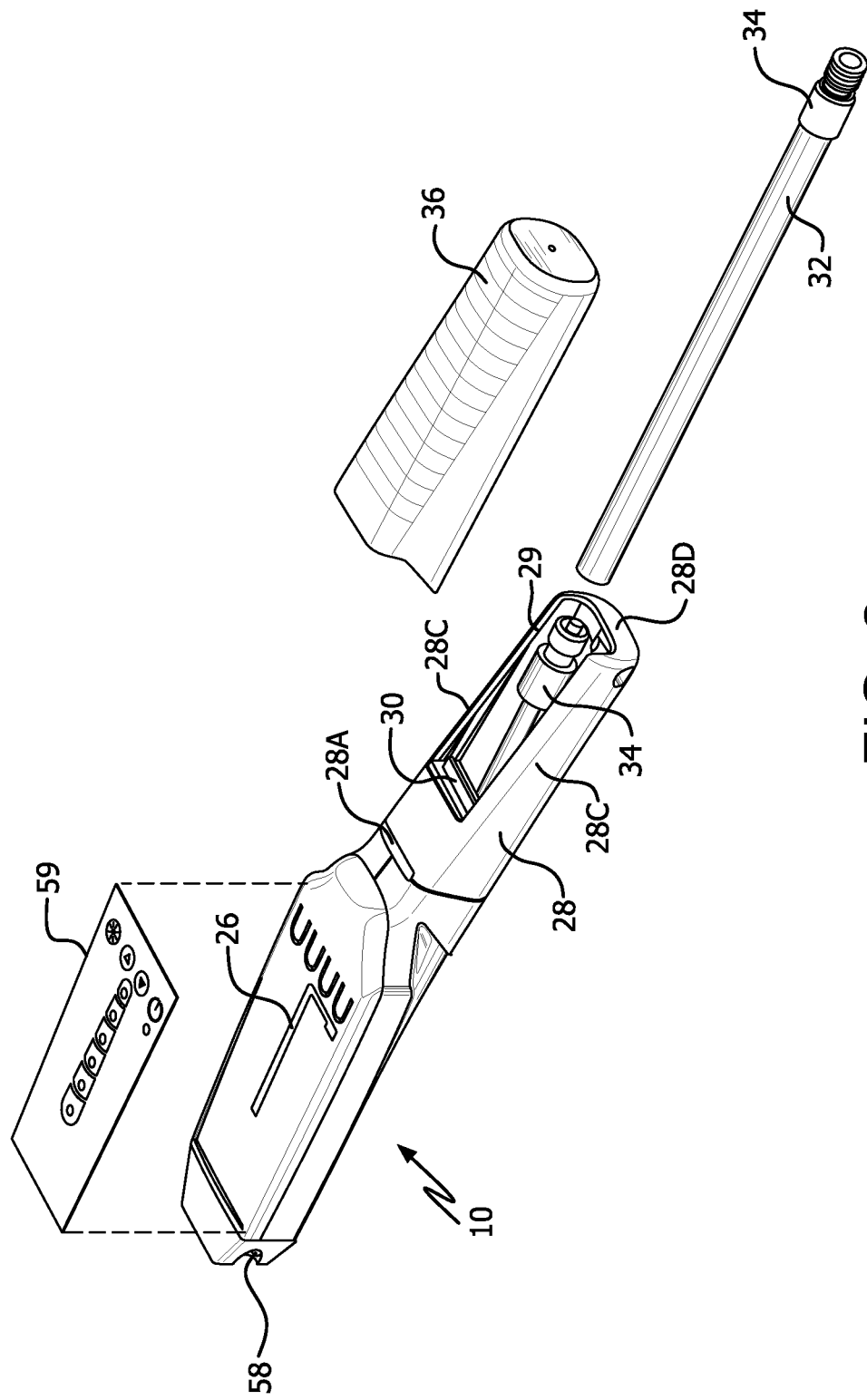
FIG. 2 is a perspective view of the probe of FIG. 1 with the probe detached and the handle cover removed.

A handle 28 is formed on a rear portion of the housing 12 and protrudes rearward from a main portion of the housing 12. The handle 28 is preferably angled slightly downwards relative to the main portion of the housing 12. The handle 28 may be formed integral with or separately attached to the main portion of the housing. As is best seen in FIG. 2, the handle 28 includes a top 28A, bottom 28B, side walls 28C and an end wall 28D which define an internal, preferably elongated storage chamber 30. As shown, an opening 29 is formed in at least a rear portion of the top 28A and preferably the end wall 28D. The opening 29 provides access to the storage chamber 30 as will become more apparent below. The chamber 30 extends through the handle and may extend into a portion of the housing 12. Alternatively, an inner front wall 31 may be included that separates the chamber from the main portion of the housing 12. One or more holes 33 are formed in the front wall.

One or more probes 32 are removably stored within the storage chamber 30 of the handle 28. As shown in FIG. 2, the probes are different. By way of example, the probes 32 shown in FIG. 2 are a contact probe and an air probe. Generally, an air probe is used to isolate leak sources in cramped places, and a contact probe is used to find gear and bearing wear in internal parts and electric motors. As shown in FIG. 2, the chamber 30 is sufficiently wide to contain two probes 32 side-by-side. The rear end of the handle 28 is sufficiently large to accommodate the base ends of probes, which may be wider than the main parts of probes. The front portions of the probes preferably extend through the hole or holes 33 in the front wall 31 and into the main portion of the housing. As shown in FIGS. 1 and 3, a handle cover 36 closes off the opening in the handle 28. The cover 36 may attach to or engage the handle in various ways. In the illustrated embodiment, the handle 28 is tapered and the cover 36 is configured to slide onto the handle 28 over the opening 29. Alternately, the cover could be detachable from or hinged to the periphery of the opening 29 and include a locking mechanism to secure the cover in the closed position.

An upper part of the storage chamber 30, under the top 28A of the handle, has a cradle 60 to receive a replaceable battery 62. The cradle 60 is mounted on rails 64 to slide between backward and forward positions. In the forward position, the battery 62 is under a solid part of the handle top 28A, and contacts on the battery connect with contacts 38 mounted on the partition wall 31 so that the battery 62 supplies power to the detector 12. In the rearward position of the cradle 60, the battery 62 projects through the opening 29, so that it can easily be removed and replaced. A commonly available square 9 volt battery (type NEDA 1604, IEC 6LR61, or similar) is suitable, because that type of battery has snap-in connectors, which may reduce the risk of the battery becoming disconnected in use. If a battery with simple applied pressure contacts is used, the cradle 60 may be provided with a latch or detent to hold it in the forward, fully inserted, position.

As an alternative, the housing 12 may contain a rechargeable battery (not shown) and the storage chamber 30 may have a connector for a recharger.

In use of the detector 10, the probes 32 are stored in the chamber 30 until they are actually needed, thereby protecting them from damage, contamination or loss. The detector 10 illustrated in the figures is extremely compact, and can easily be carried in an operative's hand, pocket, or tool bag. When the operative wishes to use the device, he or she merely needs to remove the cover 36, select and remove a desired one of the probes 32, replace the handle cover 36, attach a connector 34 on the selected probe 32 to the socket 16, insert the jack of a pair of headphones into the socket 24 if desired, and start work.

When the operative wishes to change to a different probe 32, it is merely necessary to detach the old probe 32 from the socket 16, remove the cover 36, exchange probes, mount the new probe 32 in socket 16, replace the cover 36, and continue working. The operative does not need to have immediate access to his or her tool bag, which may have been left outside the immediate working area.

Various modifications and variations can be made in the present invention without departing from the spirit or scope of the invention.

For example, in one embodiment shown in FIG. 4, a front portion 12A of the housing 12 that includes the transducer 14 may be detachable to function as a remote unit. The front portion may include a magnet or other mechanism (not shown) for attaching the front portion to a component being monitored. The front portion also includes a Bluetooth, RFID, or other wireless transmitter 70 for transmitting the signals detected by the transducer 14. The housing 12 includes a wireless receiver 72 configured to receive the signals transmitted by the transducer. This embodiment has several advantages. First, the removable front portion can be placed in locations that the entire housing 12 cannot easily reach. Second, the removable front portion can be left in position on a device being monitored when it is not being used. As such, if the sound that the operator is attempting to capture occurs infrequently, or the operator is required to make changes on the operating machinery to attempt to locate the sound and the machinery controls are at a location that is not close to the area where the sound is being monitored, the operator can leave the remote unit at the location of leak while making the changes to the machinery and still be able to detect when the sound of interest occurs.

This embodiment also allows for successive measurements to be easily taken with the remotely unit located in exactly the same place, which means that the measurements are more consistent, and changes over time in the ultrasonic signals can be detected more easily and more accurately.

Third, if the removable front portion has a battery and a (preferably non-volatile) memory, the remotely located unit can detect and store data while unattended, which data can be uploaded to the detector 10 at a later time. If the remotely located unit does not have a battery, the remote unit can be powered from the detector 10 by, for example, standard RFID techniques, although the remote unit cannot then gather data except when the detector 10 is present.

In an alternative embodiment or as an addition to any of the other embodiments, the housing 12 may include a remote electrical port (not shown) which permits a remote sensor to be electrically connected to the internal circuitry through a plug in wire. The remote sensor could be located at a place spaced apart from the housing 12 to acquire the necessary readings. The circuitry and programming in the sensor and detector 10 could be configured to permit the user to toggle between readings from the onboard sensor and the remote sensor. It is also contemplated that the onboard programming can be set to permit the user to input certain data related to the sensor(s), such as where the sensor is positioned, when it was positioned and on what equipment, thus permitting a more accurate and detailed reporting.

The remote sensor could include a memory and power source so that the data related to the sensed signals can be collected and stored on the remote sensor. The data would later be transferred to the detector what the remote is communicating with the detector (either wirelessly or through a wired connection). This permits the remote to remain in a location of interest over a period of time.

It is contemplated that a kit may be provided with multiple remote sensor units or multiple remote sensor units can be sold that have a unique unit identifier. This allows the remote units to be located in various locations on one or more machines. Along with transmitting the detected signals, the remote sensor units would also transmit the sensor unit identifier such that the detector 10 can discern which remote sensor unit is transmitting the data received.

Instead of LED indicators lights, the detector may include an LCD, LED or other type of display which can depict an alphanumeric unit identifier.

If the detector 10 is provided with a data port 24, the detector 10 preferably includes non-volatile memory and a suitable controller to store detected data until such time as the data can be downloaded.

However, a simple device in which ultrasonic signals received through a probe 32 by the transducer 24 are simply played back at audible frequency in real time through a headphone jack 24 is also very useful, and may be significantly less expensive.

It is also contemplated that the detector could take advantage of existing WiFi systems and include suitable wireless circuitry to transmit sensed signals from a remote sensor to the detector using the wireless system in the facility. Those skilled in the art would be readily capable of incorporating appropriate circuitry into the detector and remote sensor units to utilize a wireless system.

Thus, it is intended that the present invention cover the modifications and variations of this invention provided they come within the scope of the appended claims and their equivalents.

The invention claimed is:

1. An ultrasonic detector comprising: a housing containing a transducer and an electrical power supply; at least one probe capable of ultrasonic sensing; a socket at a front end of the housing into which the ultrasonic probe is removably attached so that the probe is in operative connection with said transducer for ultrasonic detection; a handle at a rear end of the housing by which the detector is holdable by a human operator in use; an elongated probe storage chamber on an inside of the housing, extending at least partially into the handle, wherein at least one of the plurality of interchangeable probes is storable within the probe storage chamber; and a cover of the handle closing a rear end of the probe storage chamber and removable to expose a portion of the probe storage chamber and allow the at least one probe to be inserted into or removed from the probe storage chamber.

2. The ultrasonic detector according to claim 1, wherein the at least one probe is a plurality of interchangeable probes, each of the probes being operatively attachable to the socket.

3. The ultrasonic detector according to claim 2, wherein the plurality of probes comprise at least a contact probe and an air probe.

4. The ultrasonic detector according to claim 2, wherein the probe storage chamber is at least sufficiently wide to contain all except one of the plurality of probes.

5. The ultrasonic detector according to claim 4, wherein the probe storage chamber is sufficiently wide to contain all of the plurality of probes.

6. The ultrasonic detector according to claim 1, wherein the housing includes at least one of a port for a battery charger, a data port for reprogramming the detector, and a battery compartment.

7. The ultrasonic detector according to claim 1, wherein the electrical power supply is a removable battery and wherein the housing includes a cradle for the removable battery, and wherein the cradle is movable between an exposed position for removing and inserting the battery and a retracted operating position.

8. The ultrasonic detector according to claim 1, wherein the power supply is a rechargeable battery mounted within the housing.

9. The ultrasonic detector according to claim 1, further comprising non-volatile data storage, a controller configured to store in the data storage detected ultrasonic signals or data derived from detected ultrasonic signals, and a data port configured to export stored data to an external device.

10. The ultrasonic detector according to claim 1, wherein the housing further includes at least one of a socket for headphones, detector touch controls, and a display.

11. The ultrasonic detector according to claim 1, further comprising a light provided at the front end of the detector and positioned to illuminate a position at or in front of a tip of a the probe when attached to the socket.

12. The ultrasonic detector according to claim 1, further comprising electronic circuitry co-operating in use with the transducer configured to control receipt of sensed signals.

13. The ultrasonic detector according to claim 1, wherein a front portion of the detector including the transducer is detachable from a rear portion of the detector that includes the handle, and the detector is operable with the front portion detached from and communicating with the rear portion.

14. The ultrasonic detector according to claim 13, wherein the front portion comprises a wireless transmitter and the rear portion comprises a corresponding wireless receiver.

15. The ultrasonic detector according to claim 1, further comprising a remote detector configured to detect ultrasonic signals when not rigidly attached to the ultrasonic detector housing, and configured to relay relevant information to the ultrasonic detector.

16. The ultrasonic detector according to claim 15, wherein the remote detector is configured to relay information to the detector through at least one of a flexible wire, a wireless transmitter, and a data store from which stored data is uploaded to the ultrasonic detector.

* * * * *